United States Patent [19]

Jessel, Jr. et al.

[11] Plant 4,884

[45] Sep. 7, 1982

[54] CHRYSANTHEMUM PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 125,139

[22] Filed: Feb. 27, 1980

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar known by the cultivar name Shamrock and particularly characterized as to uniqueness by the combined characteristics of incurved capitulum form; spider capitulum type; greenish-yellow ray floret color; diameter across face of capitulum ranging from 15 to 19 cm. at maturity; uniform ten week photoperiodic flowering response to short days; very tall plant height; and semi-upright branching pattern.

2 Drawing Figures

The present invention comprises a new and distinct cultivar of *Chrysanthemum morifolium,* Ramat., hereinafter referred to by the cultivar name Shamrock.

Shamrock is a product of a planned breeding program which had the objective of creating new chrysanthemum cultivars with spider capitulum type, greenish-yellow ray floret color, nine or ten week flowering response and with the ability to produce commercially acceptable quality in year round cut mum programs. Such traits in combination were not present in previously available commercial cultivars.

Shamrock was originated from a cross made in a controlled breeding program in Barberton, Ohio in 1970. The female parent was Nightengale (unpatented), a greenish-white spider. The male parent of Shamrock was Yellow Daisy Pot (unpatented), a yellow spooned daisy. The parentage of Nightengale and Yellow Daisy Pot are unknown to the present inventors.

Shamrock was discovered and selected as one flowering plant within the progeny of the stated cross by Walter H. Jessel, Jr. and William E. Duffett on July 22, 1971 in a controlled environment in Barberton, Ohio.

The first act of asexual reproduction of Shamrock was accomplished when vegetative cuttings were taken from the initial selection in December, 1971 in a controlled environment in Barberton, Ohio by a technician working under formulations established and supervised by Walter H. Jessel, Jr. and William E. Duffett. Continued asexual reproduction by vegetative cuttings for evaluative tests in flowering and stock programs in conjunction with horticultural examination of selected plants initiated on Nov. 30, 1977 has demonstrated that the combination of characteristics as herein disclosed for Shamrock are firmly fixed and are retained through successive generations of asexual reproduction.

Shamrock has not been observed under all possible environmental conditions. The phenotype may vary significantly with variations in environment such as temperature, light intensity and day length. The following observations, measurements and comparisons describe plants grown in Salinas, Calif. under greenhouse conditions which approximate those generally used in commercial practice.

The following traits have been repeatedly observed and are determined to be basic characteristics of Shamrock which in combination distinguish this chrysanthemum as a new and distinct cultivar:

(1) semi-incurved capitulum form, (2) spider capitulum type, (3) greenish-yellow ray floret color, (4) diameter across face of capitulum ranging from 15 to 19 cm. at maturity, (5) uniform ten week photoperiodic flowering response to short days, (6) very tall plant height (attaining a height as a flowered plant of 110 to 120 cm. from a rooted cutting given one long day week for April through November flowerings), and (7) semi-upright branching pattern.

Of the many commercial cultivars known to the present inventors, the most similar in comparison to Shamrock is the parental cultivar, Nightengale. Reference is made to attached Chart A which compares certain characteristics of Shamrock to those same characteristics of Nightengale. In general comparison to Nightengale, Shamrock has different ray floret color, shorter plant height and shorter flowering response period. The capitulum form and type and the diameter across face of inflorescence of Shamrock are similar to those same characteristics of Nightengale.

The accompanying photographic drawings show typical inflorescence and foliage characteristics of Shamrock, with colors being as nearly true as possible with illustrations of this type. Sheet 1 is a color photograph of Shamrock grown as a single stem cut disbud. Sheet 2 is a black and white photograph showing three views of the inflorescence of Shamrock.

In the following description color references are made to A Limit Color Cascade by the Munsell Company, 1972 edition. The color values were determined between 11:00 and 11:30 A.M. on Apr. 28, 1978 under 150 foot-candle light intensity at Salinas, Calif.

Classification:

*Botanical.*—*Chrysanthemum morifolium,* Ramat., cv Shamrock.

*Commercial.*—Cut spider, disbud or spray.

I. INFLORESCENCE

A. Capitulum:

*Form.*—Semi-incurved.

*Type.*—Spider.

*Diameter across face.*—15 to 19 cm.

B. Corolla of ray florets:

*General tonality (from a distance of three meters).*—Greenish-yellow, approximately 26-3 tipped with 23-4.

*Color (abaxial).*—21-4 to 23-4 (immature) oxidizing to 24-7 over 24-2.

*Color (adaxial).*—23-7 to 23-8 (immature) to 24-6 over 25-3 (mature).

C. Reproductive organs:

*Gynoecium.*—Present both ray and disc florets.

*Androecium.*—Present disc florets only; scant to none; scant to no pollen.

II. PLANT

A. General appearance:

*Branching pattern.*—Semi-upright.

*Height.*—Very tall, attaining a height of 110 to 120 cm. as a flowered plant from a rooted cutting with one long day week for April through November flowerings.

B. Foliage:

*Color (abaxial).*—Approximately 21-15.

*Color (adaxial).*—Approximately 22-13 to 22-14.

*Shape.*—Moderately lobed; slightly serrated.

CHART A
COMPARISON OF SHAMROCK AND NIGHTENGALE

| CULTIVAR | RAY FLORET COLOR | CAPITULUM FORM & TYPE | DIAMETER ACROSS FACE OF CAPITULUM |
|---|---|---|---|
| Shamrock | greenish-yellow | semi-uncurved spider | 15 to 19 cm. |
| Nightengale | greenish-white | semi-incurved spider | 15 to 19 cm. |

| CULTIVAR | PLANT HEIGHT | FLOWERING RESPONSE PERIOD |
|---|---|---|
| Shamrock | Very Tall, 110 to 120 cm. | 10 week |
| Nightengale | Very tall, 120 to 130 cm. | 11 week |

COMPARISONS MADE OF PLANTS GROWN SINGLE STEM WITH ONE LONG DAY WEEK AS IN SALINAS, CALIFORNIA.

We claim:

1. A new and distinct cultivar *Chrysanthemum morifolium,* Ramat., plant known by the cultivar name Shamrock, as described and illustrated, and particularly characterized as to uniqueness by the combined characteristics of semi-incurved capitulum form; spider capitulum type; greenish-yellow ray floret color; diameter across face of capitulum ranging from 15 to 19 cm. at maturity; uniform ten week photoperiodic flowering response to short days; very tall plant height; and semi-upright branching pattern.

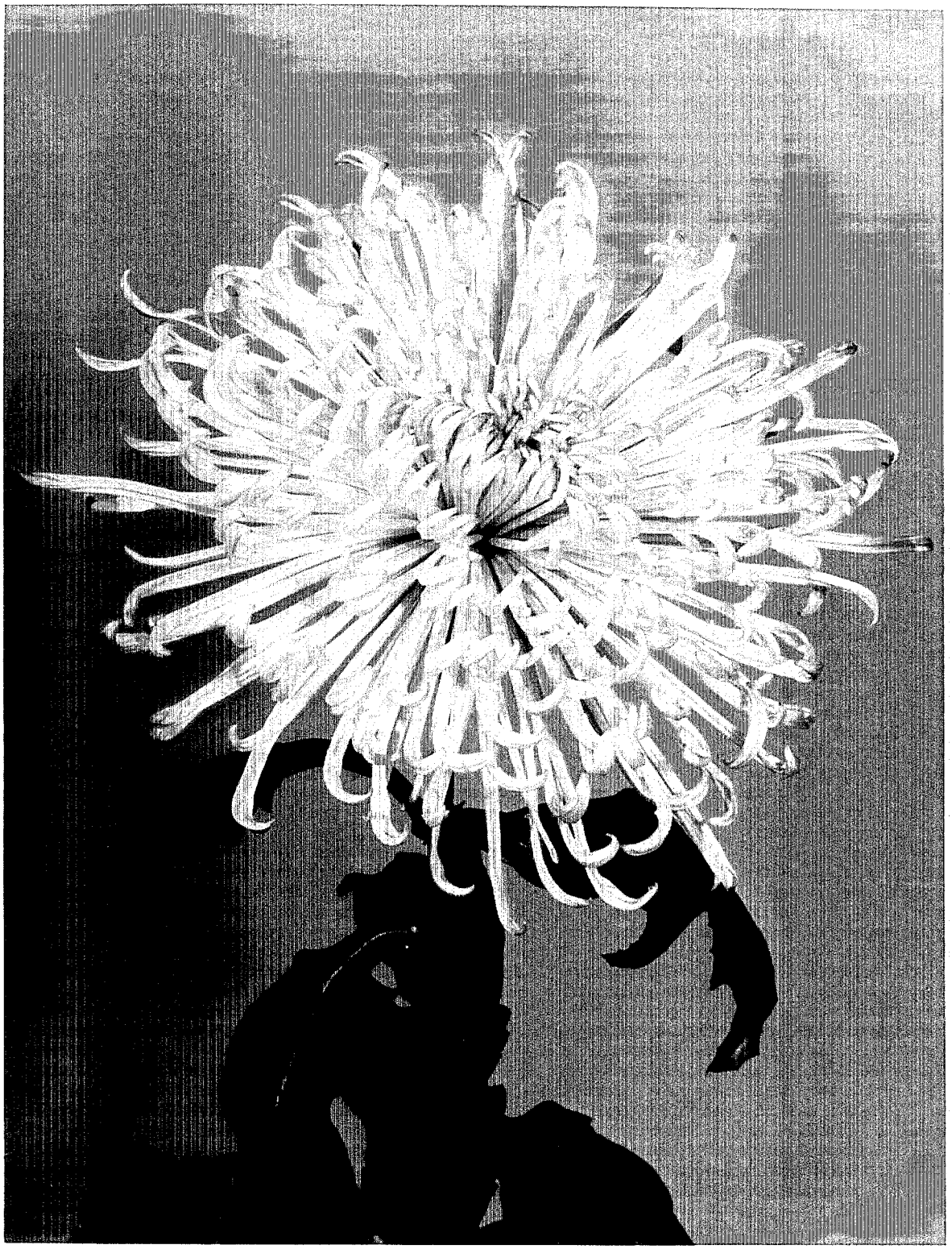

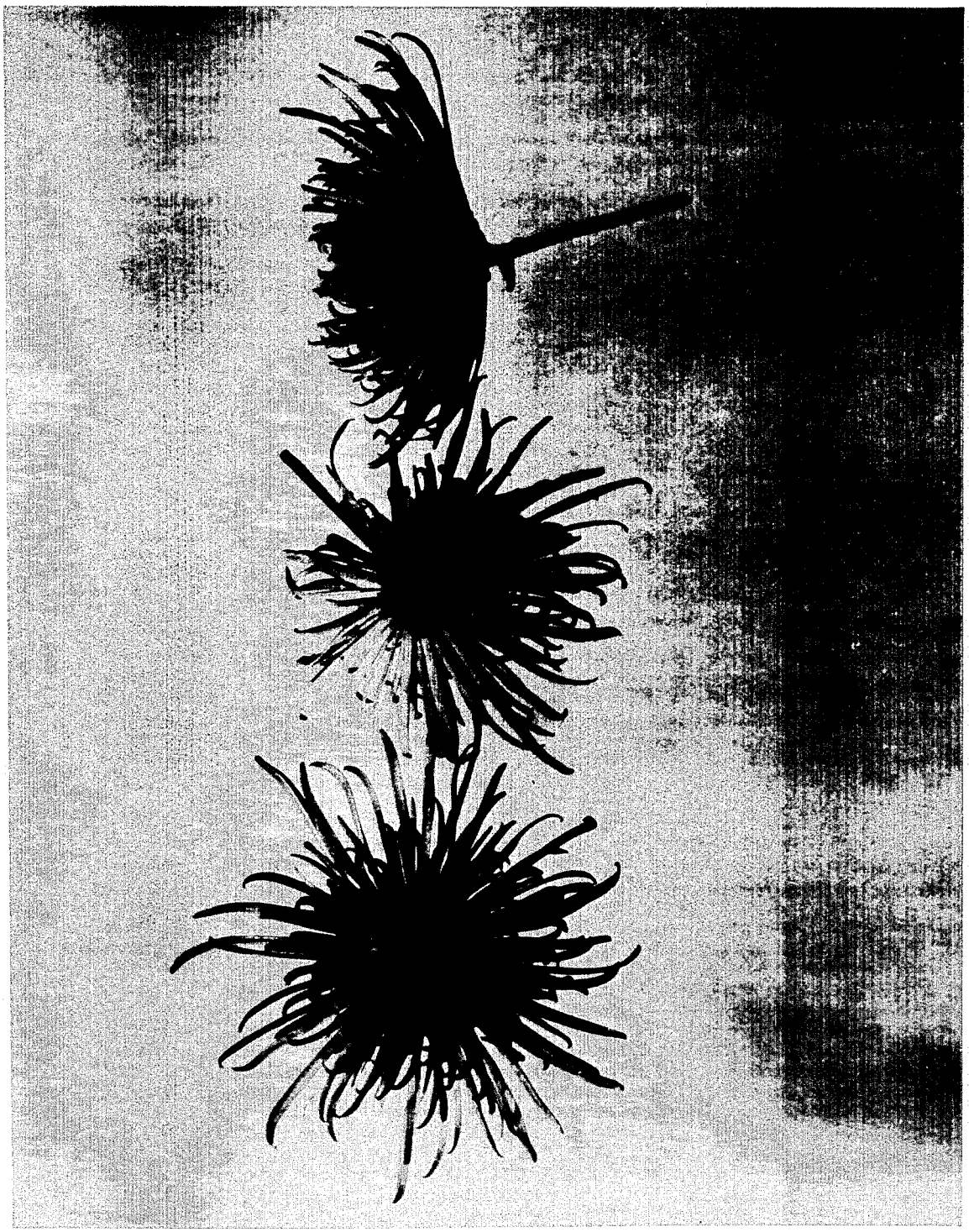

* * * * *